United States Patent [19]

Sanchez et al.

[11] Patent Number: 5,296,472
[45] Date of Patent: Mar. 22, 1994

[54] METHODS FOR DELIPIDATION OF SKIN AND CERUMEN REMOVAL

[75] Inventors: Robert A. Sanchez, Carlsbad; Sheldon S. Hendler, La Jolla, both of Calif.

[73] Assignee: Vyrex Corporation, La Jolla, Calif.

[21] Appl. No.: 40,052

[22] Filed: Mar. 30, 1993

Related U.S. Application Data

[63] Continuation-in-part of Ser. No. 805,724, Dec. 5, 1991, abandoned.

[51] Int. Cl.$^5$ .................... A61K 31/70; A61K 31/715
[52] U.S. Cl. ........................ 514/58; 514/887; 514/546; 514/859; 514/777; 514/778; 514/844; 514/846; 530/833; 424/47; 424/70; 424/71; 424/DIG. 13; 536/103
[58] Field of Search ............... 514/58, 887, 546, 859, 514/777, 778, 844, 846; 530/833; 424/47, 70, 71, DIG. 13; 536/103

[56] References Cited

U.S. PATENT DOCUMENTS

| 4,267,166 | 5/1981 | Yajima | 426/486 |
|---|---|---|---|
| 4,352,794 | 10/1982 | Koch | 514/859 |
| 4,507,319 | 3/1985 | Barratt et al. | 514/546 |
| 4,678,598 | 7/1987 | Ogino et al. | 536/103 |
| 4,869,904 | 9/1989 | Uekama et al. | 536/103 |
| 4,891,361 | 1/1990 | Hatae | 514/58 |
| 4,970,072 | 11/1990 | Honda et al. | 530/833 |
| 5,026,551 | 6/1991 | Yorozu et al. | 424/44 |
| 5,086,050 | 2/1992 | Hettche et al. | 514/887 |

FOREIGN PATENT DOCUMENTS

| 0211392 | 2/1987 | European Pat. Off. |
| 366154 | 2/1990 | European Pat. Off. |
| WO91/09962 | 7/1991 | PCT Int'l Appl. |
| WO91/09963 | 7/1991 | PCT Int'l Appl. |

OTHER PUBLICATIONS

Szejtli, J. (1985) "Cyclodextrins: A new group of industrial basic materials" *Die Nahrung* 9:911–924.
Pitha, Josef (1987) "Amorphous Water Soluble Derivatives of Cyclodextrins: From Test Tube to Patient" *Journal of Controlled Release* 6:309–313.
Pitha, Josef, et al. (1988) "Drug Solubilizers To Aid Pharmacologists: Amorphous Cyclodextrin Derivatives" *Life Sciences* 43:493–502.
Irie, Tetsumi et al. (1988) "Amorphous Water-Soluble Cyclodextrin Derivatives: 2-Hydroxyethyl, 3- Hydroxypropyl, 2-Hydroxyisobutyl, and Carboxamidomethyl Derivatives of β-Cyclodextrin" *Pharmaceutical Research* 5(11):713–717.
Pitha, Joseph (1989) "Cyclodextrins: Solutions To Insolubility" *Neurotransmissions* V(1):1–4 (published by Research Biochemicals Incorporated, Natick, Massachusetts).
Stern, Warren C. (1989) "Cyclodextrin-Based Drug Delivery" *Drug News and Perspectives* 2(7):410–415.
Strattan, Charles E. (1989) "Cyclodextrin-Based Drug Delivery" *Pharmaceutical Manufacturing International*, pp. 203–210.
Strattan, Charles E. (1991) "Chemically Modified Cyclodextrins" *Pharmaceutical Manufacturing International*, pp. 161–163.
Stratten, Charles E. (Nov./Dec. 1991) "Cyclodextrins and Biological Macromolecules", *BioPharm* pp. 44–51.
*"Gamma W8- Cyclodextrins and Derivatives", Wacker Chemicals, Promotional Literature Jun. 1990.
Uekama, "Cyclodextrin Inclusion Compounds: Effects on Stability and Bio-Pharmaceutical Properties", pp. 181–194, Elsevier Science Publishers B.V. (Biomedical Division) Topics in Pharmaceutical Sciences 1987, D. D. Breimer and P. Speiser, editors.

*Primary Examiner*—Ronald W. Griffin
*Attorney, Agent, or Firm*—Glenna Hendricks; Stephen Gates

[57] ABSTRACT

This invention relates to methods for delipidation of skin or hair through the use of cyclodextrins and cyclodextrin derivatives such as hydroxypropyl β-cyclodextrin. The invention also relates to cerumen removal methods involving introduction of cyclodextrins to the ear canal, followed by complexation of the cyclodextrin with cerumen components, and removal of the resulting cyclodextrin complexes. The cyclodextrin components are used in a substantially oil-free powdered or aqueous formulation without detergents, soaps, solvents, oils or other lipid-like agents.

10 Claims, No Drawings

METHODS FOR DELIPIDATION OF SKIN AND CERUMEN REMOVAL

CROSS REFERENCE TO RELATED APPLICATIONS

This application is a continuation-in-part application of commonly assigned patent application Sanchez et al. Ser. No. 07/805,724 filed Dec. 5, 1991, now abandonded, which is incorporated herein by reference for all purposes.

BACKGROUND OF THE INVENTION

The present invention relates generally to delipidation agents and methods of using them to prevent accumulations of lipid-like substances on mammalian skin or hair.

Humans and animals have sebaceous glands that are distributed over much of the epidermis and are associated with all or most of the hair follicles. The sebum secreted by these glands accounts for most of the lipids normally found covering the skin and hair. Sebum is composed primarily of glycerides, free fatty acids, wax esters, squalene, cholesterol esters and cholesterol in proportions that may vary greatly depending on species, ethnic background and skin type. Other glands such as the apocrine glands and sweat glands may also contribute to the lipids found on the skin and hair surfaces. The rate of sebum or lipid exudation is variable and is controlled by a number of factors including temperature and hormone balance. A number of skin disorders, notably acne and seborrhea, are associated with increased sebum production. An excessive accumulation of lipids on the skin is a common occurrence that may exacerbate problems of hygiene, body odor and general skin health.

Periodic bathing and washing with detergents or other types of suitable skin cleansers are important parts of normal skin care and the routine control of skin lipids. Beyond this level of care, it is highly desirable to have methods for the mild and effective control and removal of skin lipids for (a) cosmetic applications, to gently control skin lipid levels over extended periods of time, and to allow the application of other cosmetic agents to the skin, and (b) hygienic and medical applications, to continuously control excessive sebaceous excretions in normal or disease states, and to facilitate cleansing and medical treatment of the skin. The present invention fulfills these requirements.

Cyclodextrins and cyclodextrin derivatives have been used primarily to increase the solubility of relatively insoluble compounds and to reduce the volatility of volatile products. For example, cyclodextrin derivatives are now used for the delivery of insoluble drugs, notably steroids. They are also used to deliver pesticides, to encapsulate flavors and fragrances, to mask adverse tastes and odors, and to separate substances by selective complexation (in chromatography for example). $\beta$-cyclodextrin is now mass produced (in 1989 about 1,000 tons) and used primarily as a food flavor stabilizer. For example, a Vanillin: $\beta$-cyclodextrin complex often replaces vanillin in instant pudding mixes to slow flavor loss through evaporation during storage of the mixes on supermarket shelves.

SUMMARY OF THE INVENTION

The present invention represents a departure from the traditional uses for cyclodextrins and cyclodextrin derivatives. In this invention, cyclodextrins are used as agents for skin delipidation under gentle removal conditions. Thus, they are typically in an uncomplexed or loosely complexed state. Preferred compositions of the present invention include $\beta$- (cycloheptaamylose) and $\gamma$ (cyclooctamylose) cyclodextrins, or combinations of the two. Cyclodextrin derivatives are also often preferred. These compounds, especially 2-hydroxypropyl $\beta$-cyclodextrin, are readily available, inexpensive, and have been shown to be quite effective in delipidating skin (as shown in the examples below).

This invention is directed to a method and associated formulations for removing accumulations of lipid-like compounds from mammalian skin or hair, thus improving their overall appearance and health. These methods and formulations have the advantage of being particularly mild, non-irritating, and non-allergenic, especially in comparison to traditional detergent or lipid or organic solvent based formulations. The invention also fills a long-felt need for cosmetic formulations that remove rather than deposit lipid-like materials.

One aspect of this invention is a method including a step of applying a substantially oil-free composition to a region of skin or hair where lipids may accumulate. The composition will include a cyclodextrin having an affinity for lipid-like compounds that accumulate on mammalian skin.

According to a preferred embodiment of the invention, a substantially oil-free composition containing one or more cyclodextrin is applied to an oily region of the skin or hair. After application, the composition is preferably allowed to complex with skin lipids. Once applied, the composition may be left on the skin to continuously remove the lipid-like compounds or, alternatively, it may be washed off to cleanse skin of lipid-like compounds that have already accumulated. In the first instance, the composition may have the form and consistency of a cosmetic and can contain various additives typically found in cosmetics. In the second instance, an aqueous solution or suspension is preferred. Both procedures may be helpful in the treatment of skin disorders such as acne and seborrhea that are associated with excessive production of lipid-like compounds on mammalian skin.

The cyclodextrin(s) in the formulation will have an affinity for the lipid-like compounds that accumulate on mammalian skin and hair. In a preferred embodiment, the cyclodextrin will be hydroxypropyl $\beta$-cyclodextrin, $\gamma$-cyclodextrin, or hydroxypropyl $\gamma$-cyclodextrin. Formulations employing these cyclodextrins or other cyclodextrins will be in the form of powders, aqueous suspensions, or aqueous solutions. Substantially oil-free excipients may also be present in the formulation. Some preferred compositions will contain two or more cyclodextrins.

In a particularly preferred embodiment, aqueous cyclodextrin solutions are employed to remove cerumen from the ear canal. According to these methods, a cyclodextrin solution of between about 1 and 30% by weight is applied to the ear canal and allowed to complex with cerumen components. Most preferably, a solution of about 10% by is used. After sufficient time has elapsed to allow the cyclodextrin to penetrate and complex with the cerumen, the ear canal is rinsed to remove resulting complex. Because the cyclodextrin is provided in the form of an aqueous solution, it is easy to apply to and remove from the ear canal. And unlike commercially available products, it also does not leave a sticky, oily residue in the ear.

A further understanding of the details and advantages of this invention may be obtained by reference to the detailed description that follows.

DESCRIPTION OF THE PREFERRED EMBODIMENT

The following definitions are presented to aid in understanding the present invention but are not intended to limit the meaning in the claims. The specific embodiments are only examples of items within broader classes.

"Cyclodextrin" refers to $\alpha$, $\beta$, or $\gamma$-cyclodextrins and derivatives of these compounds. Included in this definition are alkyl, ether, ester, polymeric or other derivatives of cyclodextrins.

"Substantially oil free" means the present composition contains less than about 10% by weight total of a lipid, oil, wax, fatty acid or other oil-like substances. Preferably, less than about 2% of any of these materials will be present in the formulations of this invention. Most preferably, the formulation will be completely free of any oil, wax, or other lipid-like compound.

"Lipid-like compound" refers to many compounds that accumulate on mammalian skin, including any of a number of substantially non-polar compounds. These compounds are typically secreted by the sebaceous, apocrine, and sweat glands. Examples include glycerides, free fatty acids, wax esters, squalene, cholesterol esters and cholesterol.

"Delipidation" describes a process in which lipid-like compounds are sequestered or removed from an area such as a region of skin. This may be accomplished by, for example, complexing with a cyclodextrin component.

"Guest molecules" are compounds which complex with the cyclodextrin ring. Typically, they will reside in the hydrophobic cavity of a cyclodextrin component ring. These compounds may be loosely or strongly complexed with the cyclodextrin. Examples include drugs, flavor enhancers, and a variety of non or slightly-polar molecules.

"Affinity for lipids" describes the tendency of a cyclodextrin or other material to form stable complexes with lipids and lipid-like compounds such as those secreted from mammalian sebaceous, apocrine and sweat glands. Cyclodextrins or cyclodextrin derivatives having such affinity will typically bind with lipids or oily substances. For example, the cyclodextrin may be in an aqueous environment where it is substantially uncomplexed. In this situation, a cyclodextrin having an "affinity for lipids" will preferentially complex with lipids. Alternatively, the cyclodextrin may be in an environment where it is loosely complexed with one or more guest molecules. Such cyclodextrin will have an "affinity for lipids" if it readily exchanges the guest molecule or molecules with non-polar, lipid-like substances accumulating on mammalian skin. In some cases, the guest molecule may remain complexed with the cyclodextrin after the lipid-like compound enters.

The present invention provides novel methods for controlling the excessive buildup of sebum and other oily, lipid, and lipid-like materials on mammalian, and particularly human, skin or hair. In one embodiment, a cyclodextrin is used to continuously remove oils that build up on the skin over a period of time. In another embodiment, a cyclodextrin containing composition may be used for periodic cleansing of the skin or hair. In either instance, the active agent used in the methods of this invention is a cyclodextrin, cyclodextrin derivative or a mixture thereof. The cyclodextrin-based material will complex with lipids and other non-polar substances typically found on mammalian skin or hair, thus preventing or removing an excessive accumulation of oils.

Cyclodextrins, previously known as Schardinger dextrins, are ring structures composed of glucose molecules linked together by $\alpha$-1,4 glycosidic linkages much like starch. Cyclodextrin has $\alpha$, $\beta$, and $\gamma$ structures corresponding to molecules having 6, 7, and 8 glucose residues respectively. The diameters of cyclodextrin cavities are 5.2 angstroms for $\alpha$-cyclodextrin, 6.4 angstroms for $\beta$-cyclodextrin, and 8.3 angstroms for $\gamma$-cyclodextrin. This range in cavity sizes accommodates a wide range of "guest" molecule sizes. It appears, however, that $\beta$-cyclodextrins and $\gamma$-cyclodextrins accommodate the broadest range of biologically important lipids, including steroids, fatty acids and glycerides. $\beta$ and $\gamma$-cyclodextrins and their derivatives are therefore preferred in this invention.

Cyclodextrins have several properties that make them particularly beneficial for hygienic application. They are naturally occurring, non-toxic, neutral, odorless, non-irritating, chemically stable, and available in bulk.

Cyclodextrins are prepared from starch (i.e. linear dextrins) by a well-known enzymatic process described in W091/09962 which is hereby incorporated by reference for all purposes. Briefly, partially hydrolyzed starch is acted upon by cyclodextrin-transglycosyl transferase—produced by various microorganisms such as *Bacillus macerans* or *Bacillus circulans*—to produce cyclodextrins.

Cyclodextrins possess a bifunctional chemistry that provides the unique properties necessary to practice the present invention. The outside of the ring is hydrophilic, laden with hydroxyl groups, while the interior is hydrophobic. The interior cavities bind many organic solvents and lipophilic substances. Hence, nonpolar molecules or slightly polar molecules having nonpolar regions that can fit comfortably within the hydrophobic ring sometimes form soluble complexes with cyclodextrins. In addition to binary cyclodextrin guest complexes, ternary complexes may form if the cyclodextrin ring is sufficiently large. Multiple complexes containing more than one cyclodextrin ring may also form.

In aqueous solutions, the somewhat nonpolar cyclodextrin interior is occupied by energetically unfavored water molecules (polar-nonpolar interaction) which are readily replaced by less polar guest molecules such as lipid-like compounds. The cyclodextrin/guest complexation is driven by substitution of the high-enthalpy water molecules by the less polar guest. Since the cyclodextrin molecule is a two-dimensional ring, the entry of nonpolar molecules is typically a fast process. The entry phenomenon is known as either inclusion complexation or host-guest complexation. If the size of the guest molecule is too small or too large for the cavity, the binding between the guest molecule and the cyclodextrin will be relatively weak.

Cyclodextrin complexes containing even sparingly soluble nonpolar compounds are often more soluble in aqueous environments than are the uncomplexed compounds. Cyclodextrins are not, however, ideal solubilizers since their crystallinity limits water solubility. In order to improve the solubility of the cyclodextrins while preserving their complexing properties many derivatives such as polymers, esters and ethers have been synthesized and studied. The most common and widely used of these derivatives is the commercially available poly(2-hydroxypropyl) ether (available from American Maize Products Company, Hammond, Ind. and other suppliers), usually called hydroxypropyl $\beta$-cyclodextrin. This compound is typically prepared by reacting $\beta$-cyclodextrin with propylene oxide in aqueous alkali. Other derivatives include 2-hydroxyethyl and 2,3-dihydroxypropyl cyclodextrin as well as various other alkyl group containing derivatives.

The cyclodextrin containing formulations of the present invention may be powders, solutions, suspensions or slurries. They also may be applied in creams, pastes, gels, solutions, overlays and sprays. These formulations will contain, at most, small quantities (no more than 10% and preferably less than 2% by weight) of detergents, organic solvents, oils, waxes, latexes and other lipid-type agents that are now commonly used for skin cleansing purposes. In preferred embodiments, such components will be absent from the formulation.

A powdered cyclodextrin-containing formulation may be employed where loose contact with the skin is desired. For example, if the cyclodextrin is to be excluded from small pores of the skin, powder formulations should be employed. Such formulations may simply contain pure powdered cyclodextrin or cyclodextrin derivative. Alternatively, the formulations may contain powdered or granular additives that improve the product's appearance, texture, or odor. Extenders, such as talc, pigments, and fragrances may be added. Other agents such as those that improve the flowability of the product (i.e. prevent clumping or packing) may also be added. Still other suitable additives include salts, buffers, and antimicrobial agents.

Where more intimate skin contact is necessary, the cyclodextrin or cyclodextrin derivative may preferably be provided as an aqueous suspension or an aqueous solution. These preparations will generally be preferred in cleansing applications. Typically, the aqueous formulations will contain greater than 5% by weight of cyclodextrin component. Most preferably, greater than 10% cyclodextrin component will be present. Some chemically modified cyclodextrins such as the hydroxyalkyl derivatives described above are particularly preferred in aqueous solution formulations because of their high solubility. In any form, the non-polar interior of the cyclodextrin ring should remain available to the external environment, and lipids in particular. Typically this is not a problem because the cyclodextrin cavity is bilaterally accessible, allowing fast entry of non-polar molecules.

Cyclodextrin formulations of the present invention may also be used to delipidate hairshafts and the surrounding skin (e.g. the scalp). Preferably, an aqueous solution of the cyclodextrin component will be used in a rinse or shampoo. Other components such as fragrances, pigments, and gelling agents may be included as well. Any additive should be selected based on its ability to not interfere with the delipidating properties of cyclodextrin.

Whether powdered or aqueous, the cyclodextrin is the primary active ingredient of compositions used in this invention. Preferably, non-polar solvents, waxes or other additives such as lipids will be present only in low concentrations. Most preferably, these materials will be absent from the formulation. In addition, detergents and other agents which tend to dry the skin should be present in, at most, low concentrations. Typical cosmetic compositions contain any or all of the above undesirable materials, including oils and fats. Many of these additives will complex with the cyclodextrin, thus rendering it wholly or partially ineffective for removing sebum from skin. Detergents may, in addition, severely dry and irritate the skin and in some individuals cause allergic reactions.

Present methods of delipidation often include the use of non-aqueous solvents (such as ethyl alcohol and acetone) and witch hazel, all of which may be irritating and astringent. Such materials penetrate the epidermal barrier and remove lipids from beneath the barrier, which is undesirable. Cyclodextrins do not significantly penetrate the epidermal barrier. Thus, cyclodextrin compositions are particularly beneficial in treating the skin of patients that are susceptible to irritation, allergy and infection. Preferred compositions of this invention will be free of or substantially free of skin-irritating agents such as astringents, detergents, or organic solvents.

Other cosmetic components may, however, be added to the basic cyclodextrin powder or aqueous formulation without adversely affecting its delipidation properties. Many of these are listed in a standard formulation text such as Remington's Pharmaceutical Sciences (Mack Publishing Co., 1985) which is incorporated herein by reference. Typically additives will include fragrances, pigments, pH buffers, antimicrobial agents and texture and appearance enhancing substances. Each of these can be added to improve the appeal of the formulations. In addition, thickeners and gelling agents such as glycols and carboxymethyl cellulose may be added. Preferred additives will not be harsh, abrasive, or allergenic and will not excessively dry sensitive skin. Additives should be carefully chosen from among compounds that will not avidly bind with the cyclodextrin ring. Otherwise, the lipid complexing function of the cyclodextrin may be diminished. In general, the additives should be either somewhat polar and thus "uncomfortable" in the non-polar interior of the cyclodextrin ring or sufficiently large that they can not complex with the cyclodextrin molecule.

The formulations contemplated by the present invention may be applied in a variety of manners. Typically, they will be applied in any manner that a modern cosmetic formulation is applied. However, they may also be applied as cleansing agents. Preferred methods include brushing, dabbing on with a sponge, or rolling on. In some instances, a pack or other paste formulation may be desired. In addition, a spray type application may be useful. Typically, the cyclodextrin formulation will remain in place long enough to delipidate the skin. Since each individual's skin produces differing amounts of different oils, effective delipidation will require different lengths of contact time.

Numerous benefits are associated with the use of cyclodextrins as contemplated by the present invention. The overall appearance and health of the skin and hair will generally be enhanced by delipidation. Thus, many individuals without skin disorders can benefit by normal delipidation according to this invention. Individuals who use excessive amounts of soaps, moisturizers and astringents sometimes experience "rebound oiliness" in which the skin produces extra lipids to counteract dryness. The mild delipidating activity of the present invention is an effective alternative to the sometimes harsh effects of soaps and astringents.

Cyclodextrins, unlike linear dextrins, are rather resistant to common amylolytic enzymes present in microorganisms of the human skin. Thus, the cyclodextrin compositions of this invention will not promote infection and can be used to help in the treatment of certain skin disorders such as acne, seborrhea, seborrheic dermatitis (oily form), acne rosacea, and male pattern baldness associated with increased oiliness of the skin. Because the severity of these conditions varies from individual to individual, the amount of cyclodextrin applied and the frequency of application will likewise vary. The physician will take this into account when prescribing a cyclodextrin treatment regimen.

Cerumen (ear wax) is another type of lipid that can accumulate and cause health problems. Cerumen is a heterogeneous mixture of cell debris, hair, dirt, and various lipid-like substances which include cholesterol and cholesterol esters, ceramides, long chain fatty acids, squalene, wax esters, and glyceryl esters. The exact composition varies from patient to patient.

Excessive cerumen can become impacted in the ear canal and be difficult and painful to remove. It can also lead to ear infections. The method of the present invention can be used to soften and remove excessive accumulations of cerumen from the ear and can help in treating ear infections that may be associated with increased production of cerumen. Preferably, aqueous solutions or suspensions of between about 1 to 30% by weight cyclodextrin are used in the cerumen removal formulations of this invention. More preferably, solutions of between about 5 and 20%, and most preferably about 10% by weight cyclodextrin are used. Of course, other additives can provided as describe elsewhere herein. Further, a powder or granular formulation may be preferred in some instances. Especially preferred compositions are those that are substantially or completely free of skin-irritating agents such as lower alcohols or astringents.

In many embodiments, the cyclodextrin will be, $\beta$-cyclodextrin, $\gamma$-cyclodextrin, or hydroxypropyl $\beta$-cyclodextrin, or hydroxypropyl $\gamma$-cyclodextrin. However, other forms of cyclodextrin may be advantageously employed to remove cerumen (and other bodily lipid-containing compositions). Because cerumen includes a heterogeneous mixture of lipid-like substances, a heterogenous mixture of cyclodextrins having different cavity sizes may be advantageously employed. Thus, compositions containing, for example, compounds having $\beta$- and $\gamma$-cyclodextrin cavities may be advantageously employed in the present invention. If some of the cerumen components are not adequately complexed by $\beta$-cyclodextrin, they may be complexed by $\alpha$ or $\gamma$-cyclodextrins.

According to this invention, the cyclodextrin composition is applied to the ear canal where it penetrates the cerumen and complexes with some or all of the lipid components to form cyclodextrin complexes. The cyclodextin can be applied as ear drops or other convenient method. After sufficient time has elapsed to allow the cyclodextrin component to penetrate and complex with the cerumen, the resulting complex is removed from the ear canal. This can be accomplished by a variety of techniques, including removal with a swab, rinsing/washing with water, and absorption with tissue.

The present invention may also be used to delipidate skin before various procedures are performed. For example, preoperative delipidation of a surgical site can be accomplished with a cyclodextrin. In addition, precleaning of the skin before application of trichloroacetic acid (TCA) for a facial peel is necessary to increase the effectiveness of the procedure. The use of cyclodextrins according to the present invention will fill this need.

Because the cyclodextrin compositions of the present invention absorb oil under relatively mild conditions, they are ideal for helping in the treatment of disorders in which the skin is sensitive or already irritated. HIV infected individuals, and particularly AIDS patients are susceptible to skin infections and irritations. Sensitive skin is defined as skin which is fragile, delicate, and reacts with certain cosmetics and fragrances. Typically, sensitive skin is defenseless against such environmental factors as weather changes and the sun.

EXPERIMENTAL

Example 1 Simulation Experiment; Dissolution Of Skin Lipids

Sebum and other skin lipids were collected from facial skin by gentle scraping with a spatula. Small amounts of the lipid were applied to glass slides as thin smears, approximately 50 ug/20 mm$^2$. One slide (A) was covered with a water layer, and another (B) was covered with a 5% solution of hydroxypropyl-$\beta$-cyclodextrin (American Maize Products Company, Hammond, Ind.) in water. The slides were shaken gently periodically at room temperature, and examined by transmitted light. No obvious changes were observed on the lipid smear of slide A. Slide B showed evidence of some dispersal of lipid within a few minutes. After 30 minutes most of the lipid phase was gone and the aqueous phase remained clear. Water strongly tended to separate away from the lipid layer in slide A, but showed no tendency to separate from the lipid layer of slide B.

This experiment was repeated using cerumen collected from the ear. Identical results were obtained.

Example 2 Simulation Experiment; Absorotion Of Lipids

Glass slides containing thin smears of skin lipids were prepared as in example 1. Slide A was an untreated control. Powdered $\beta$-cyclodextrin (Calbiochem Corp., La Jolla, Calif.) was placed over the lipid layer of slide B and gently pressed down with a flat spatula, without any triturating or mixing action. After 5 minutes at room temperature, both slides were gently rinsed several times with distilled water. Both were covered with water and examined by transmitted light. Slide A appeared to be substantially unchanged, and the film showed a strong repellency of water. Only a trace of film remained on slide B, and no repellency of water was noted.

Example 3 Skin Test

A female applied a very thin layer of $\beta$-cyclodextrin polymer in water suspension (American Maize Products Company, Hammond, Ind.) to one side of the face and nose. The suspension applied smoothly and easily and gave a sensation of coolness. Within several minutes and for a period of 4–6 hours thereafter, the treated skin was oil-free as judged by appearance (no shiny or moist look) and texture.

Example 4 Skin Test

A male applied a very thin layer of powdered beta-cyclodextrin (Calbiochem Corp., La Jolla, Calif.) to one side of the face and nose, using his finger. The powder applied smoothly and easily. The white powder was no longer visible after several minutes. Over the next two hours in a warm room, the treated areas appeared to be oil-free, both visually and texturally. The untreated areas had a shiny appearance and a moist, oily texture.

The test was repeated with powdered hydroxypropyl-$\beta$-cyclodextrin (American Maize Products Co., Hammond, Ind.) and similar results were obtained.

Example 5 Skin Test

A male applied a thin layer of powdered hydroxypropyl-$\beta$-cyclodextrin (American Maize Products Co., Hammond, Ind.) to one side of the face and nose. After several minutes, the face was gently sprayed with water. As compared to the untreated areas, the treated areas tended to wet much more easily and uniformly, with almost no "balling" of the water into droplets, indicative of a greatly reduced lipid content.

Example 6 Cerumen Complexation

Multiple equivalent samples of cerumen were prepared as follows. Ear wax from several patients were collected and combined in water by ultrasonication. The resulting suspension was coarsely filtered to remove hair and large particles. Aliquots of the suspension were then spotted onto polyethylene sheets and dried with warm air to form a yellowish waxy cerumen layer. The polyethylene sheets were cut into disks, each containing about 7 milligrams of cerumen.

The disks were placed in three different tubes containing different formulation: tube 1 contained a 10% by weight aqueous solution of $\gamma$-cyclodextrin (Wacker Chemicals USA, Inc., New Canaan, Conn.); tube 2 contained a composition of urea peroxide, water, glycols and other components (Debrox from Marion Merrell Dow, Cincinnati, Ohio); and tube 3 contained a composition of peptide oleate condensate and propylene glycol (Cerumenex from Purdue Frederick, Norwalk, Conn.). In each tube, the disk was completely submerged in the solution. The compositions in tubes 2 and 3 were highly viscous and oily.

After approximately 10 minutes, there was no noticeable degradation of the cerumen in either tubes 2 or 3. The cerumen remained affixed to the polyethylene disks even after swirling. Further, the yellowish color of the cerumen remained unchanged. In tube 2, small bubbles formed which were apparently oxygen resulting from peroxide decomposition.

After approximately 10 minutes, the cerumen in tube 1 (containing the cyclodextrin composition), had begun to separate from the plastic backing and its color had lightened. Further, some cerumen complex had accumulated at the bottom of the tube. This indicated that the cyclodextrin had permeated through the cerumen fill. On swirling the tube, the cerumen completely separated from the polyethylene backing and disintegrated into the aqueous solution.

Example 7 Cerumen Complexation With Different Cyclodextrins

Smears of about 0.5 mg of cerumen/10mm $^2$ were placed side-by-side on glass slides and observed under a stereoscopic microscope. On each smear, 50 microliters of water or a solution of cyclodextrin (2% by weight in water) was deposited. In the smears treated with water, cerumen broke into particles which remained undissolved. In the smears treated with cyclodextrin solutions, the cerumen broke apart faster and began to dissolve after several minutes. This effect was observed with alpha-, gamma-, and hydroxypropyl-beta-cyclodextrins.

Example 8 Cerumen Removal In Human Patients

The cerumen removing actions of Debrox, Cerumenex (see Example 6) and a 10% solution of $\gamma$-cyclodextrin in water were compared in two patients. In each patient, the $\gamma$-cyclodextrin solution was tested in one ear, and then one of the other agents was tested in the other ear. Each solution was tested as follows: the solution was warmed to body temperature, and then the ear canal was filled with 20–30 drops. After 10 minutes, the solution was drained from the ear canal into a clear cup. An otoscope was used to examine the canal before and after the treatment. Debrox and Cerumenex produced very little change in the nature and quantity of the wax deposits in the ears. The recovered solutions from the ears were substantially clear. The patient who received Cerumenex reported some irritation of the ear canal later in the day.

The application of the 10% $\gamma$-cyclodextrin solution resulted in substantial reduction in the amount of wax in the ears. The recovered solutions were very cloudy, and consisted of suspensions of clearly visible particles. No irritation was reported by either patient.

Example 9 Cerumen Removal In An AIDS Patient

A 10% solution of $\gamma$-cyclodextrin in water was applied to the ear canals of an AIDS patient. The ears were substantially cleared of wax, and the recovered solutions were cloudy with cerumen particles. No irritation was reported by the patient.

The use of uncomplexed cyclodextrins to remove cerumen from AIDS patients or other immune-compromised patients is particularly advantageous. AIDS patients and HIV infected individuals in general are particularly susceptible to skin irritation and infections. In fact ear and sinus infections are among the leading causes of morbidity in AIDS patients. Thus, the effective, yet mild methods of the present invention are useful in minimizing the risk of serious ear infections in AIDS patients.

CONCLUSION

In conclusion, the methods and formulations of the present invention have been shown to be effective in delipidation of mammalian skin and hair. While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of removing cerumen from the ear canal comprising the steps of:
   (1) instilling a composition containing as an active agent a cerumen permeating and complexing effective amount of substantially uncomplexed cyclodextrins;
   (2) allowing said composition containing cyclodextrin to remain in the ear canal for sufficient time for said composition to permeate cerumen, and
   (3) removing said composition containing cyclodextrin with complexed cerumen from the ear canal.

2. The method of claim 1 wherein the cyclodextrin is $\beta$-cyclodextrin.

3. The method of claim 2 wherein the cyclodextrin is hydroxypropyl β-cyclodextrin.

4. The method of claim 1 wherein the composition comprises two or more cyclodextrins having different cavity size.

5. The method of claim 4 wherein the cyclodextrins are selected from the group consisting of α-cyclodextrins, β-cyclodextrins and γ-cyclodextrins.

6. The method of claim 1 wherein the cyclodextrin includes more than one type of cyclodextrin.

7. A method of claim 1 wherein the cyclodextrin is present in a substantially oil-free solution at between about 1% and 30% by weight.

8. A method of claim 1 wherein the cyclodextrin-containing composition consists essentially of cyclodextrin in water.

9. A method of claim 8 wherein the cyclodextrin is selected from the group consisting of a α-cyclodextrins, β-cyclodextrins and γ-cyclodextrins.

10. A method of claim 8 wherein the composition contains cyclodextrins of at least two different cavity sizes.

* * * * *